(12) United States Patent
Nakamura

(10) Patent No.: US 8,123,791 B2
(45) Date of Patent: Feb. 28, 2012

(54) PATCH FOR FACILITATING BLOOD CIRCULATION

(75) Inventor: Shunsuke Nakamura, Aichi (JP)

(73) Assignee: Nakamura Co., Ltd., Ama-Gun (JP)

( * ) Notice: Subject to any disclaimer, the term of this patent is extended or adjusted under 35 U.S.C. 154(b) by 1180 days.

(21) Appl. No.: 11/851,450

(22) Filed: Sep. 7, 2007

(65) Prior Publication Data

US 2008/0255645 A1  Oct. 16, 2008

(30) Foreign Application Priority Data

Apr. 16, 2007 (JP) .................. 2007-002673

(51) Int. Cl.
*A61F 7/02* (2006.01)
*F24J 1/00* (2006.01)
(52) U.S. Cl. ........ 607/108; 607/104; 607/109; 607/110; 607/112; 607/114; 126/263.01
(58) Field of Classification Search .......... 607/108–114; 126/265.01, 265.02
See application file for complete search history.

(56) References Cited

U.S. PATENT DOCUMENTS

| | | | | |
|---|---|---|---|---|
| 6,893,453 | B2 * | 5/2005 | Agarwal et al. ............... | 607/108 |
| 2006/0160455 | A1 * | 7/2006 | Sugyo et al. .................. | 442/417 |
| 2007/0277806 | A1 * | 12/2007 | Dodo ....................... | 126/263.02 |

FOREIGN PATENT DOCUMENTS

| | | |
|---|---|---|
| CN | 2 248 550 Y | 3/1997 |
| CN | 1 433 789 A | 8/2003 |
| EP | 1 923 447 | 5/2008 |
| JP | 08-310962 A1 | 11/1996 |
| JP | 3069710 U | 4/2000 |
| JP | 2002-226390 | 8/2002 |
| WO | 2007/018211 | 2/2007 |

OTHER PUBLICATIONS

XP-002496372.
XP-002219113.

* cited by examiner

*Primary Examiner* — Roy Gibson
(74) *Attorney, Agent, or Firm* — Burr & Brown

(57) ABSTRACT

A patch for facilitating blood circulation, including a warmer, a powder-containing bag and a base sheet. The warmer includes iron powder for generating heat oxidized by oxygen in the air and an oxidization regulatory agent enclosed in a flat, air permeable bag. The outer shape of the bag is larger than that of the warmer, and contains powder including components contained in bamboo vinegar or wood vinegar. The outer shape of a base sheet is larger than that of the bag, and the base sheet has an air ventilation hole at a central portion. An adhesive layer is formed on the surface of one side of the base sheet. The warmer and the powder-containing bag are sequentially adhered onto the adhesive layer to cover the air ventilation hole.

7 Claims, 6 Drawing Sheets

PATCH FOR FACILITATING BLOOD CIRCULATION

BACKGROUND OF THE INVENTION

1. Field of the Invention

The present invention relates to a patch for facilitating blood circulation, the patch being used by adhering it onto an affected area for the purpose of facilitating blood circulation.

2. Description of the Prior Art

A patch for facilitating blood circulation, and which contains components that are effective in terms of the facilitation of blood circulation, has been conventionally widely known in Japan. In recent years, bamboo vinegar and wood vinegar have in particular been noted as components that are effective in terms of the facilitation of the blood circulation. Bamboo vinegar is a liquid obtained by cooling gas that is generated at the time that bamboo is carbonized and comprises 80-90% of water and 10-20% of organic compounds. Although the main component of the bamboo vinegar is acetic acid, other components such as acids, phenols, carbonyls are also contained in it as trace elements. Moreover, wood vinegar is a liquid that is similar to the above-described bamboo vinegar obtained from gas generated at the time that charcoal is manufactured. In both types of vinegar, acetic acid is the main component, and a strong degree of acidity is accordingly prevalent.

Patches for facilitating blood circulation, patches into which bamboo vinegar or wood vinegar has been absorbed, and which patches are attached to a base material as an effective component, have been disclosed in publications such as Japanese Patent No. 2903293 in the Official Gazette. Moreover, a sheet for facilitating blood circulation in cases where wood vinegar is distilled by heat at a high temperature, and in which only portion remaining within a range of from 98° C. to 103° C. are absorbed and dried in a dextrin powder, and in which this dried powder is then enclosed within a sheet in a bag form, has also been disclosed in Japanese Registered Utility specification No. 3069710 in the Official Gazette.

However, since the above-described conventional patches contemplate have been intended to facilitate blood circulation by gradually stimulating components that are effective in terms of facilitating blood circulation by means of a rise in body temperature at a time when the patches are adhered onto affected areas, a problem has arisen that the capacity of patches to provide an immediate effect has been extremely modest.

SUMMARY OF THE INVENTION

An object of the present invention is therefore to solve the conventional problems described above and to provide a patch for facilitating blood circulation that does have a capability of providing an immediate effect and which can stimulate the facilitation of blood circulation immediately at a time that it is adhered onto an affected area.

A patch for facilitating blood circulation that has been prepared for the purpose of achieving the object of the present invention comprises a warmer in which both an iron powder generating heat oxidized by oxygen in the air and an oxidization regulatory agent are enclosed in the interior of a flat bag that possesses air permeability, a powder-containing bag in which a powder containing a component such as bamboo vinegar or wood vinegar and that facilitates blood circulation is contained in a flat bag whose outer shape is larger than that of the warmer, and a base sheet which is larger than the above-described powder-containing bag and which is equipped with a hole for ventilation of air at a central portion.

In this patch for facilitating blood circulation a adhesive layer has been formed on the surface of one side and the patch is sequentially adhered in such a way that the above-described warmer and the powder-containing bag cover the air ventilation hole.

Before the patch is used, the surface of a adhesive layer of the base sheet is covered by means of an adhesive sheet that can be peeled off. Moreover, the warmer is contained in the interior of a bag that does not possess air permeability. However, at the time that the patch is used, the adhesive peel off sheet is peeled off, the adhesive layer of the base sheet is exposed, the warmer and the powder-containing bag are sequentially adhered onto the adhesive layer, and are adhered onto the affected part by use of a adhesive layer that extends to the exterior, rather than to the outer boundary, of the powder-containing bag. Then, since not only the powder-containing bag is precisely adhered and maintained in a state such that the powder-containing bag is in contact with the affected area, but also the warmer adhered onto the base sheet is exposed to the outer air through the air ventilation hole, the warmer generates heat by utilizing oxidization heat with which oxygen in the air oxidizes the iron powder, and thus makes the affected area warm. The powder-containing bag is accordingly heated within a short time, and in consequence the component for facilitating blood circulation inside the powder-containing bag is absorbed via the skin, body fluid is absorbed and then the blood circulation of the affected area is facilitated by means of warming on the part of the warmer. Blood circulation in the affected area is rapidly facilitated by these synergic effects. Moreover, since the warmer does not directly make contact with the affected area as a result of the inner surface of the warmer being concealed by the powder-containing bag, a product with a high level of reliability in terms of safety becomes possible, and there is no danger of burns.

It should be noted that as a powder-containing bag, it is preferable that use be made of a mixture containing dextrin and a dried powder, in which a component that is effective in terms of facilitating blood circulation and that is contained in bamboo vinegar or wood vinegar has been absorbed into the carrier in a powder form, and that this mixture be enclosed in a bag having air permeability, or that both the component that is effective in terms of facilitating blood circulation contained in bamboo vinegar or wood vinegar and other components with beneficial pharmaceutical effect be absorbed in the carrier in powder form.

Moreover, it is preferable that when the warmer is used, or also when it is sold, the warmer contained in the interior of the bag having air permeability, the powder-containing bag and the base sheet whose surface has been covered by the adhesive peel-off sheet all be in one set, and that one set, or a plurality of sets, be put in advance into a sealed bag.

DETAILED DESCRIPTION OF THE INVENTION

Hereinafter, a preferable mode for performing the present invention will be explained in detail on the basis of the drawings.

Figure 3:
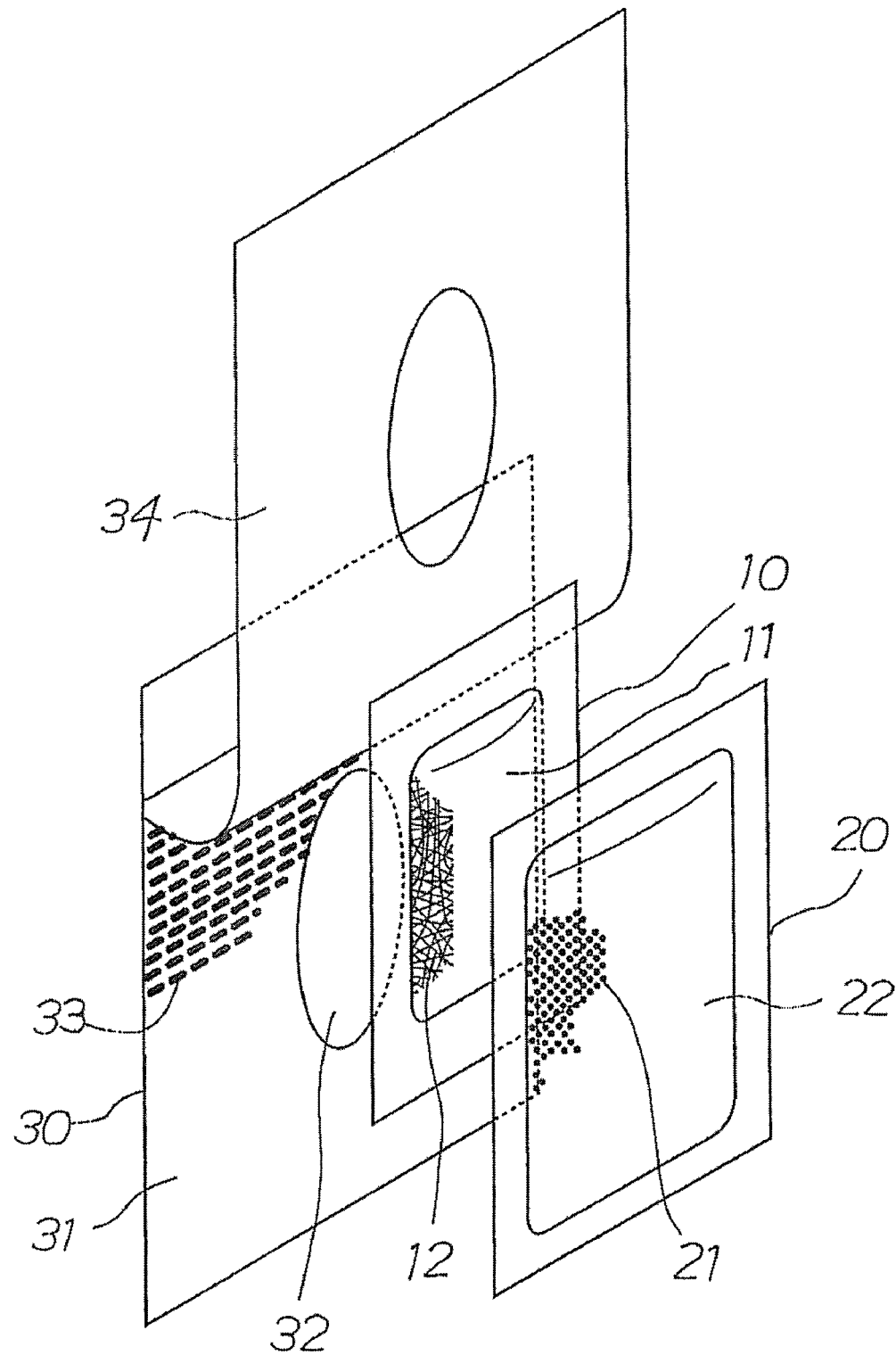
FIG. 3 is a perspective view of the state where the adhesive peel-off sheet is being peeled off.

As shown in FIG. 3, a patch for facilitating blood circulation according to the present invention is constituted by the warmer 10, the powder-containing bag 20 and the base sheet 30.

The warmer 10 is referred to in Japan as a "disposable body warmer", in which heat resulting from oxidation of iron powder has been utilized, and in which in the interior of a flat bag 11 having air permeability, an iron powder 12 which generates the heat oxidized by oxygen in the air and an oxidization regulatory agent are enclosed.

The powder-containing bag 20 is a bag in which a powder 21 containing the components that are effective in terms of facilitating blood circulation and that are contained in bamboo vinegar and wood vinegar are contained in a bag 22 made of a substance such as an unwoven fiber or paper.

The base sheet 30 is a sheet in which the surface of one side of the sheet body 31 is made up of a adhesive layer 33 and that has been covered by means of an adhesive peel-off sheet 34 in a state before it is used an on which an air ventilation hole 32 has been formed at a central portion of the sheet body 31.

Figure 2:
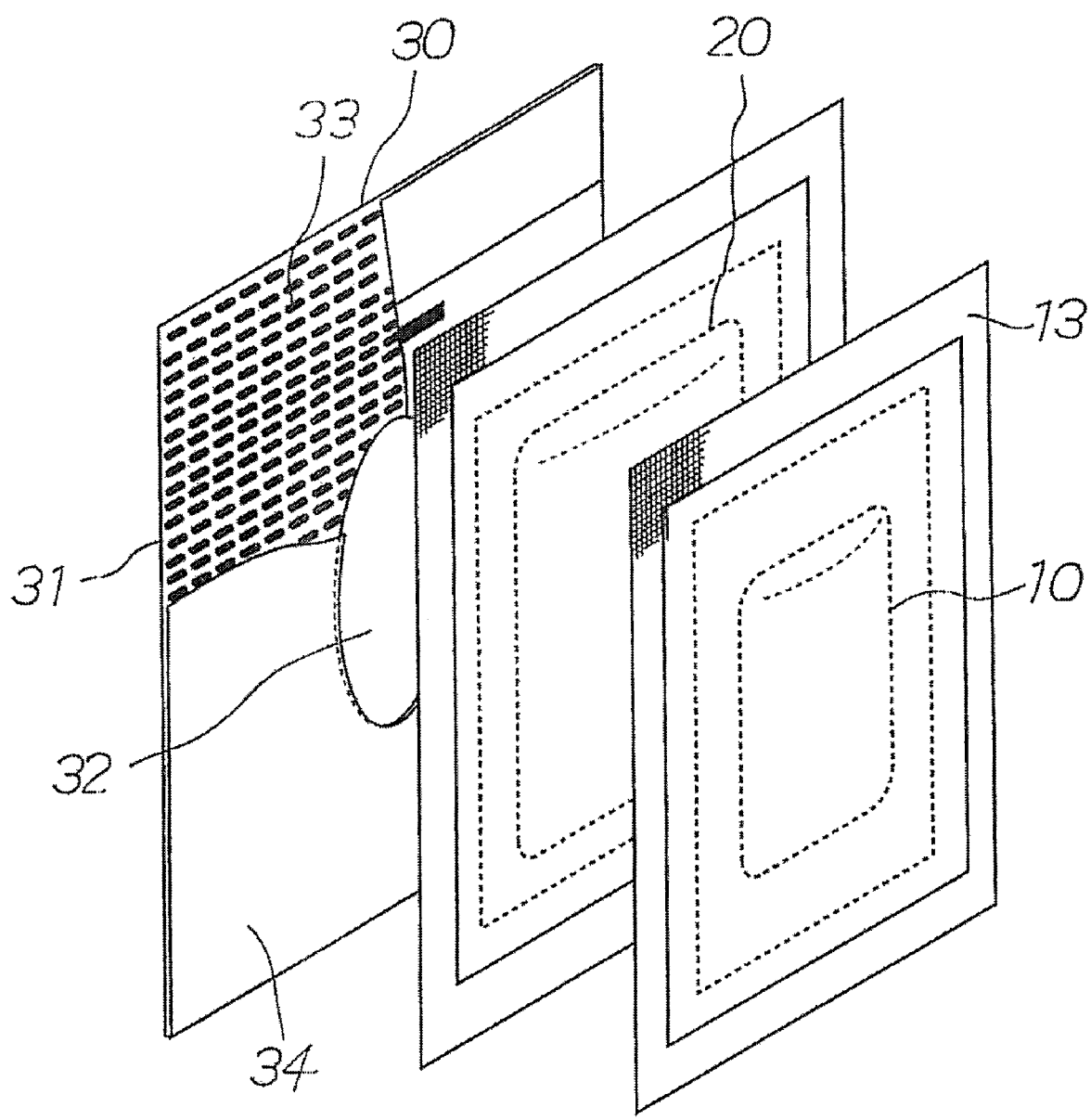
FIG. 2 is a perspective view of a state existing before the use of a patch for facilitating blood circulation of the present invention.

The warmer 10 described above is a bag in which the interior of the bag 11 is of a flat shape and made of paper having air permeability, for example, having a size of an outer shape of about 60 mm×50 mm, and in which in addition to the iron powder 12 oxidization regulatory agents such as an activated carbon, wood powder, vermiculite, common salt are enclosed. An example of the composition is as follows. Iron powder: 60 mass percent, Activated carbon: 8 mass percent, Vermiculite: 8.5 mass percent, NaCl: 3.5 mass percent, Water: 20 mass percent. The bag 13, which is enclosed so as to be impermeable to air before it is used, as shown in FIG. 2, in such a way as to prevent generation of heat by means of oxidization before it is used. As the above-described warmer 10, for example, a product which is available on the market by the trade name of Hokaron-mini manufactured by Lotte Health Industries, Co., Ltd. can be utilized. The above-described warmer 10 gradually oxidizes the iron powder 12 by means of oxygen in the air penetrating through the bag 11 having air permeability when the warmer is taken out from the bag that is impermeable to air 13, and can accordingly maintain a predetermined temperature over a predetermined period of time by means of the oxidization heat.

The above-described powder-containing bag 20 is a bag in which powder 21 containing the components that are effective in terms of facilitating blood circulation, components contained in bamboo vinegar and wood vinegar, has been contained within a flat and square-shaped bag 22 having, for example, a size of about 70 mm×60 mm so that its outer shape is larger than that of the above-described warmer 10. It is preferable that the powder-containing bag 20 be made in such a way that the reversed surface of the surface adhered onto the base sheet 30 of the powder-containing bag 20, that is, the surface which is in contact with the affected area, be made air permeable, and that the components that are effective in terms of facilitating blood circulation can easily stimulate the affected area.

In concrete terms, the powder 21 is a powder made up of a mixture of dextrin and dried powder in which the components that are effective in terms of facilitating blood circulation, and that are contained in bamboo vinegar and wood vinegar, have been absorbed into the carrier in a powder form.

Moreover, the powder 21 can be a powder in which a powder made up of a mixture of dextrin and between a dried powder in which the components that are effective in terms of facilitating blood circulation, and that are contained in bamboo vinegar and wood vinegar, have been absorbed with other components having beneficial pharmaceutical effects and in which the mixture has then been occluded. As other components having beneficial pharmaceutical effects, one or several species selected from a rice bran enzyme, an extract from the leaf of Houttuynia cordada, an extract from a pepper, an extract from the leaf of a loquat, a chitosan granule and an ascorbic acid can all be used.

As a preferable example of the blending of the powder 21, 100 portions (referred to as portions by mass) of a 3 to 5-fold condensed liquid of bamboo vinegar and wood vinegar at which a part or the greater part of tar portions and alcohol portions has been removed, 15-20 portions of vegetable cellulose as a carrier in a powder form, 60-80 portions of dextrin and, as and when appropriate, suitable amounts of one or several species selected from a rice bran enzyme, an extract from the leaf of Houttuynia cordada, an extract from a pepper, an extract from the leaf of a loquat, a chitosan granule and ascorbic acid, which are the other beneficial pharmaceutical components are blended and then regulated. As the above-described powder 21, a powder such as, "Kinomegumi" (trade name), which is manufactured by "Kinomegumi Honpo" and which is available on the market, can for example also be used.

The base sheet 30 is a sheet in which the air ventilation hole 32 has been formed at the center of the sheet body 31 and the whole of one side surface of the sheet body 31 has also been made the adhesive layer 33. In a state before it is used, the adhesive layer 33 has been covered with the adhesive peel-off sheet 34. The base sheet 30 has an outer shape whose size is larger than that of the powder-containing bag 20 described above; for example the outer shape can be about 120 mm×90 mm, and at the central portion an air ventilation hole 32 having a size of about 60 mm×50 mm in a rectangular window shape has been provided and arranged.

Figure 1:
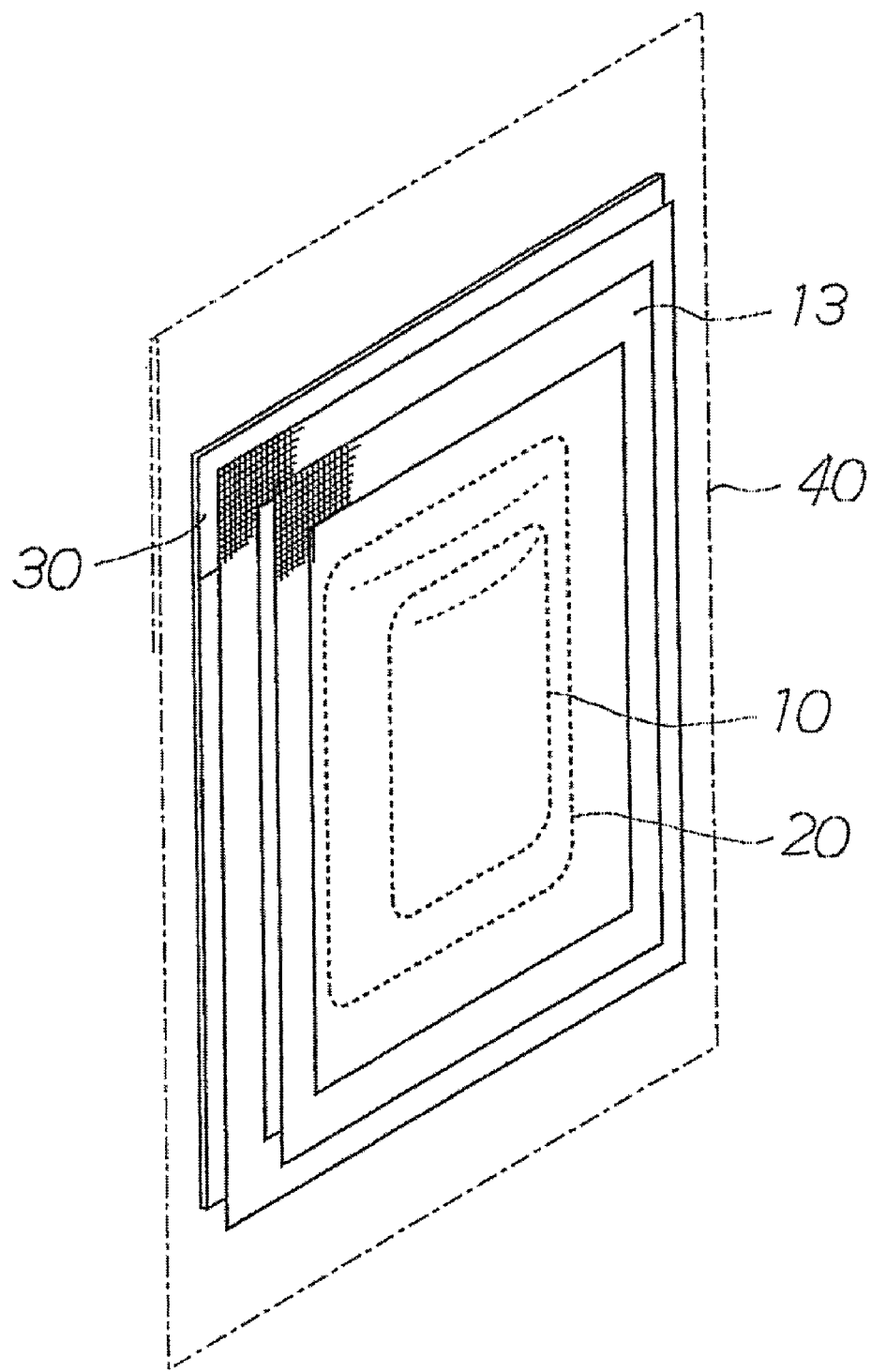
FIG. 1 is a perspective view of a packaging state of a patch for facilitating blood circulation of the present invention.

The above-described warmer 10, the powder-containing bag 20 whose outer shape is larger than the warmer 10 and further, the base sheet 30 whose outer shape is larger than that of the powder-containing bag 20 are individually packaged in an outer packaged bag 40 as a set and as a portion for use on a single occasion, as shown in FIG. 1, in a state in which only the warmer 10 has been enclosed in the bag 13 that is impermeable to air. Alternatively, a plurality of sets can be packaged in advance in the outer packaged bag 40 as portion for use on a plurality of times use. It is more preferable that in the interior of the outer packaged bag 40, in addition to and in combination with, the items described above, a wet tissue or the like be also incorporated, for purposes of wiping dirt from the affected area.

Figure 4:
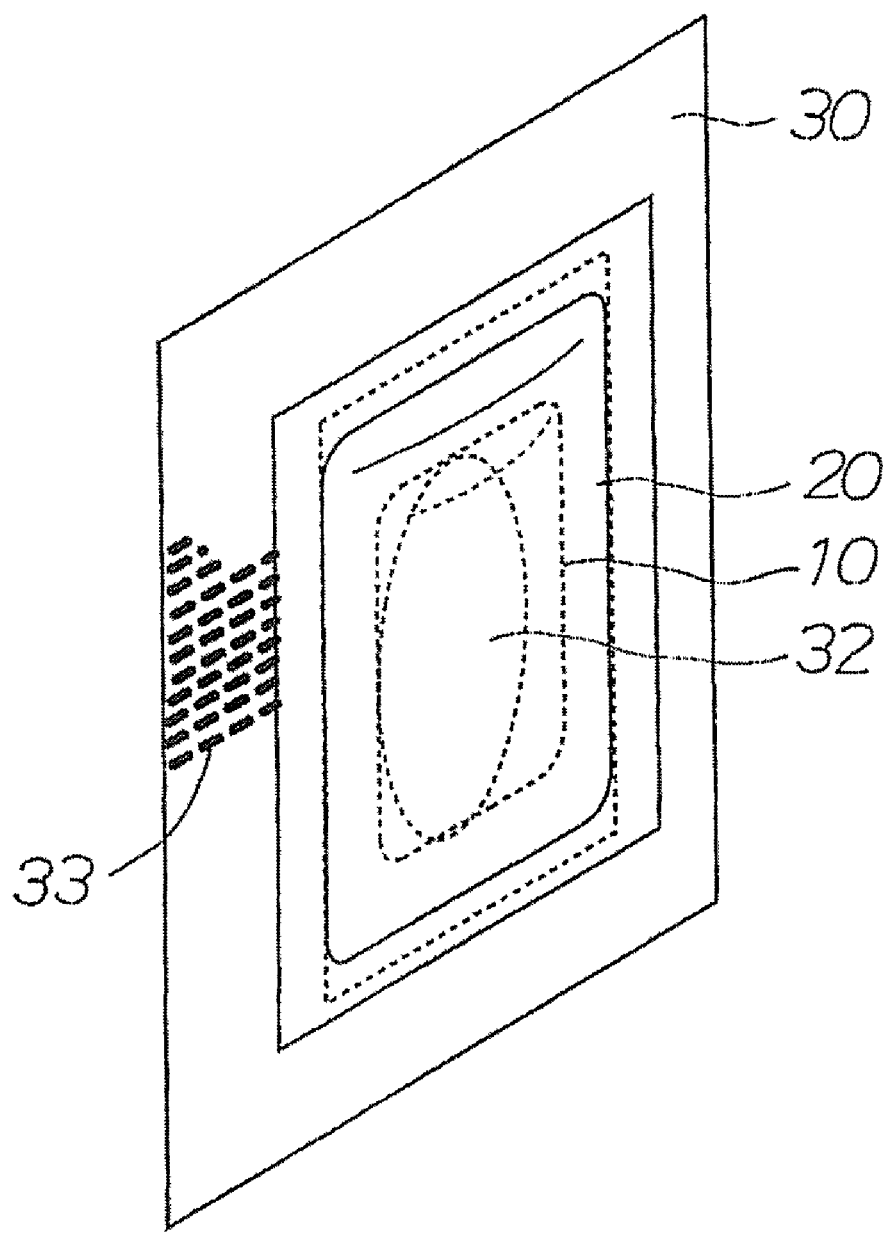
FIG. 4 is a perspective view of a state in which a warmer and a powder-containing bag have been adhered onto the base sheet.
Figure 5:
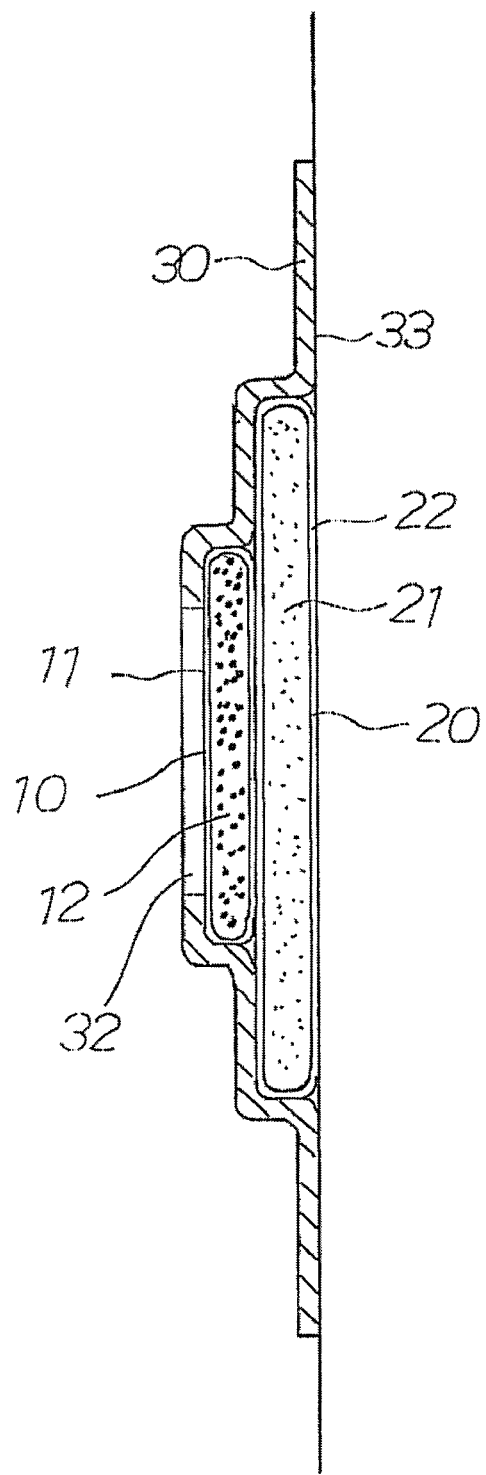
FIG. 5 is a cross sectional view of a diagram of FIG. 4.
Figure 6:
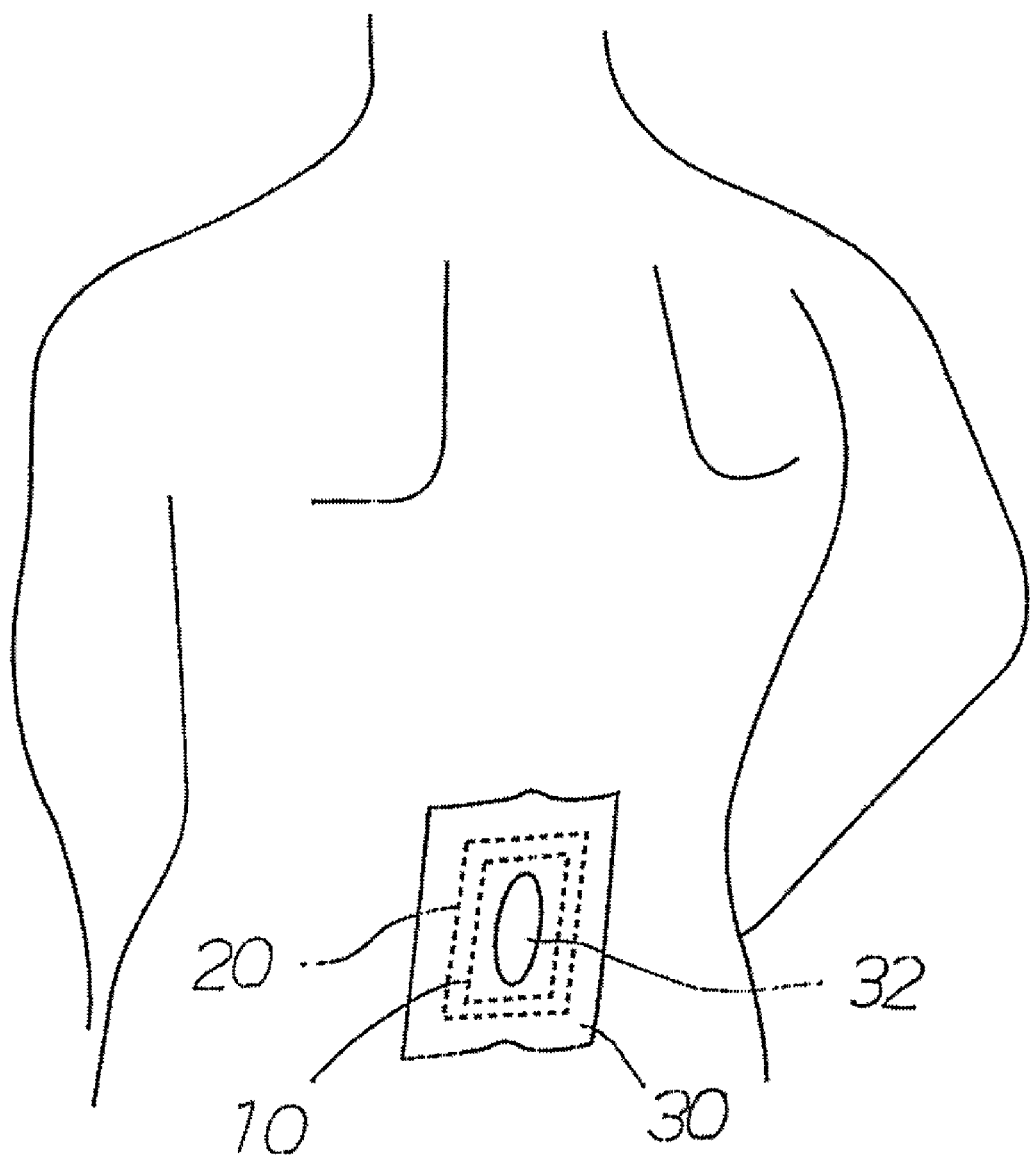
FIG. 6 is a constitutional diagram showing a state in which a patch has been adhered onto an affected area.

At times of use, the warmer 10, the powder-containing bag 20 and the base sheet 30 are first taken out from the outer packaged bag 40, as shown in FIG. 2, the adhesive peel-off sheet 34 is peeled off, as shown in FIG. 3, and the adhesive layer 33 of the base sheet 30 is exposed. The warmer 10 is then adhered in such a way that it covers the air ventilation hole 32, and further, the powder-containing bag 20 is adhered from above. These states are shown in FIGS. 4 and 5. Since the outer shape of the powder-containing bag 20 is larger than that of the warmer 10, it is possible for it to be adhered from over the warmer 10 and for its outer boundary to be adhered onto the adhesive layer 33. Moreover, since the outer shape of the base sheet 30 is even larger than that of the powder-containing bag 20, the adhesive layer 33 on its outer boundary can be utilized and adhered onto an affected area. The procedures are illustrated in FIGS. 5 and 6.

As is clearly illustrated in FIG. 5, the warmer 10 faces the air ventilation hole 32 of the base sheet 30, the warmer 10 generates heat by means of oxygen in the air penetrating into it, and the powder-containing bag 20 which is in contact with the warmer is rapidly heated. As a result, the components that are effective in terms of facilitating blood circulation are absorbed via the skin, and blood circulation in the affected area is also facilitated by means of heating on the part of the warmer.

It should also be noted that the inner surface of the warmer 10 is concealed by means of the powder-containing bag 20, that the warmer 10 does not directly touch the affected area, and that there is no danger of burns. Moreover, adhesion to the affected area can be also easily performed by means of utilizing the outer boundary of the adhesive layer 33.

The invention claimed is:

1. A patch for facilitating blood circulation comprising:
   a warmer comprising an iron powder and an oxidization regulatory agent that are enclosed in an interior of a flat bag that is air permeable, wherein the iron powder generates oxidization heat when exposed to oxygen in the air;
   a powder-containing bag having an outer shape that is larger than that of the warmer and containing a powder including components for facilitating blood circulation mixed with at least one of bamboo vinegar and wood vinegar; and
   a base sheet having an outer shape that is larger than that of said powder-containing bag with an air ventilation hole at a central portion thereof, said base sheet comprising an adhesive layer formed on a surface of one side thereof, wherein said warmer and said powder-containing bag are sequentially adhered to said base sheet in such a way that said warmer and said powder-containing bag cover the air ventilation hole.

2. The patch for facilitating blood circulation according to claim 1, further comprising an adhesive peel-off sheet that covers the surface of the adhesive layer of the base sheet and said adhesive peel-off sheet is removed before said patch is used.

3. The patch for facilitating blood circulation according to claim 1, wherein the warmer that has been adhered onto the base sheet is exposed to external air through the air ventilation hole.

4. The patch for facilitating blood circulation according to claim 1, wherein said patch is made in such a way that the base sheet on which the warmer and the powder-containing bag are sequentially adhered on an affected area by the portion of the adhesive layer of the base sheet which extends outside the outer boundary of the powder-containing bag.

5. The patch for facilitating blood circulation according to claim 1, wherein the powder-containing bag is air permeable and the components for facilitating blood circulation comprise a mixture of dextrin and a dried powder component that is contained in the bamboo vinegar or wood vinegar and is absorbed into a carrier in a powder form.

6. The patch for facilitating blood circulation according to claim 1, wherein the components for facilitating blood circulation are a powder and further comprise one or more other beneficial pharmaceutical components selected from the group consisting of a rice bran enzyme, an extract from a leaf of Houttuynia cordada, an extract from a pepper, an extract from a leaf of a loquat, a chitosan granule and an ascorbic acid in a carrier in a powder form.

7. The patch for facilitating blood circulation according to claim 1, wherein a surface that is opposite to the surface that is adhered onto the base sheet of the powder-containing bag has air permeability.

\* \* \* \* \*